United States Patent [19]  [11] 4,420,613
Uhrhan et al.  [45] Dec. 13, 1983

[54] DIHYDROBENZOTHIAZINE COMPOUNDS AND THE PREPARATION THEREOF

[75] Inventors: Paul Uhrhan, Odenthal; Edmund Krauthausen, Cologne; Kurt-Rainer Stahlke, Kuerten; Gerwolf Quaas, Cologne; Lothar Ruetz, Dormagen, all of Fed. Rep. of Germany

[73] Assignee: Bayer Aktiengesellschaft, Leverkusen, Fed. Rep. of Germany

[21] Appl. No.: 358,891

[22] Filed: Mar. 17, 1982

[30] Foreign Application Priority Data

Mar. 24, 1981 [DE] Fed. Rep. of Germany ....... 3111513

[51] Int. Cl.$^3$ .................. C07D 279/16; C07D 417/06; C07D 417/14
[52] U.S. Cl. ......................................... 544/51; 544/52
[58] Field of Search ..................................... 544/51, 52

[56] References Cited

U.S. PATENT DOCUMENTS 3,661,927  5/1972  Zivkovic .............................. 544/51

FOREIGN PATENT DOCUMENTS 1620308  3/1970  Fed. Rep. of Germany .
576969   6/1976  Switzerland .

*Primary Examiner*—John M. Ford
*Attorney, Agent, or Firm*—Connolly and Hutz

[57] ABSTRACT

The present invention relates to new dihydrobenzothiazine compounds, to the production thereof and to the use thereof as stabilizers and co-stabilizers against the oxidative and/or thermal degradation of organic polymers.

7 Claims, No Drawings

DIHYDROBENZOTHIAZINE COMPOUNDS AND THE PREPARATION THEREOF

This invention relates to new dihydrobenzothiazine compounds, to the production thereof and to the use thereof as stabilisers and co-stabilisers against the oxidative and/or thermal degradation of organic polymers.

It is known that many organic polymers, such as polyolefins, ABS-polymers and various rubber-like polymers, undergo degradation under the effect of heat, oxygen, ozone and/or light during storage and processing. Products produced from organic polymers of this type are similarly affected in practical applications. Such degradation gives rise to a deterioration in physical properties, for example to discolouration, clouding, surface crazing, and to a deterioration in mechanical properties, for example tensile strength. To avoid this, it is conventional practice to add stabilisers.

The most effective oxidation inhibitors are amine-based compounds, for example p-phenylene diamine derivatives or oligomeric 2,2,4-trimethyl-1,2-dihydroquinoline. However, they discolour the products stabilised therewith and result in more or less pronounced contact discolouration (J. Voigt "Die Stabilisierung der Kunststoffe gegen Licht und Warme (The Stabilisation of Plastics against Light and Heat)," Springer-Verlag, Berlin/Heidelberg/New York, 1966, cf. in particular pages 279 to 316). For this reason, amine stabilisers may only be used to a limited extent in practice, for example in vehicle tyres, while the less effective phenolic stabilisers are used on a much wider scale.

Accordingly, there is a need for non-discolouring oxidation inhibitors comparable in effectiveness with amine-containing stabilisers.

In general, phenolic and amine-containing oxidation inhibitors adversely affect cross-linkable polymers because the radical cross-linking process is disturbed by the transfer of hydrogen atoms. This results in partial inactivation of the oxidation inhibitors. Added to this is the fact that cross-linked polymers are more sensitive to oxidation than uncross-linked polymers because they still contain long-lived radicals (which serve as starter radicals for the thermo-oxidative ageing process) and an increased concentration of readily oxidisable groups. Accordingly, although the effectiveness thereof is reduced by the cross-linking reaction, the oxidation inhibitors have to meet fairly stringent requirements. However, any increase in the concentration of oxidation inhibitor also leads to fairly serious interference with the cross-linking process with the result that it is difficult to produce adequately stabilised polymers characterized by a high degree of cross-linking.

The compounds corresponding to general formula (I) according to the present invention are non-discolouring stabilisers comparable in effectiveness with amine-containing oxidation inhibitors. They do not adversely affect the cross-linking of cross-linkable polymers, particularly polyolefins.

The compounds according to the present invention correspond to the following general formula (I):

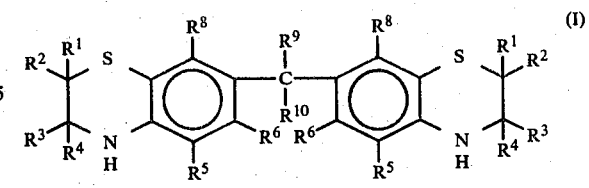

wherein
$R^1$ and $R^2$, which may be the same or different, each represents hydrogen, lower alkyl containing from 1 to 4 carbon atoms, cycloalkyl containing from 5 to 8 carbon atoms, aralkyl containing from 7 to 11 carbon atoms or aryl or together represent a radical $-(CH_2)_m-$ wherein m represents an integer of from 4 to 7;

$R^3$ and $R^4$ which may be the same or different, each represents lower alkyl containing from 1 to 4 carbon atoms, optionally substituted cyclohexyl containing from 5 to 8 carbon atoms, aralkyl containing from 7 to 11 carbon atoms or aryl or together represent a radical $-(CH_2)_n-$ wherein n represents an integer of from 4 to 7, or one of the radicals $R^3$ or $R^4$ together with $R^1$ or $R^2$ represents an alkylene radical containing from 3 to 6 carbon atoms;

$R^6$ and $R^8$, which may be the same or different, each represents hydrogen, halogen, nitro, linear or branched alkyl containing from 1 to 12 carbon atoms, linear or branched alkenyl containing from 2 to 12 carbon atoms, aralkyl containing from 7 to 11 carbon atoms, cycloalkyl containing from 5 to 8 carbon atoms, and the radicals $R^5$ are the same or different and represent hydrogen, halogen, nitro, linear or branched alkyl containing from 1 to 12 carbon atoms, linear or branched alkenyl containing from 2 to 12 carbon atoms, cycloalkyl containing from 5 to 8 carbon atoms, aralkyl containing from 7 to 11 carbon atoms, alkoxy, the radical

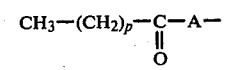

wherein
p represents an integer of from 0 to 20, preferably from 8 to 16 and
A represents $-(CH_2)_q-$, $-O-(CH_2)_q-$, $-NH-(CH_2)_q-$ or $-S-(CH_2)_q$ wherein q=0 to 4, preferably 0 or 1, or the radical

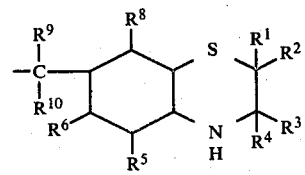

wherein
$R^1$ to $R^6$ and $R^8$ are as defined above, while $R^9$ and $R^{10}$ represent the radicals defined below, and $R^9$ and $R^{10}$ independently represent hydrogen, optionally substituted aryl, linear or branched alkyl containing from 1 to 12 carbon atoms, cycloalkyl or cycloalkenyl containing from 5 to 8 carbon atoms or $R^9$ and $R^{10}$ together with the carbon atoms to which they are attached complete a cycloalkyl radical containing from 5 to 7 carbon atoms.

Independently of one another, $R^1$ and $R^2$ preferably represent hydrogen or a lower alkyl radical containing from 1 to 4 carbon atoms, $R^3$ and $R^4$ represent a lower alkyl radical containing from 1 to 4 carbon atoms and $R^5$ to $R^8$ represent hydrogen, $R^9$ and $R^{10}$ are as defined above.

More preferably, $R^1$ and $R^2$ independently represent hydrogen or methyl, $R^3$ and $R^4$ independently represent methyl and $R^5$ to $R^8$ independently represent hydrogen.

The following are examples of compounds corresponding to the present invention:

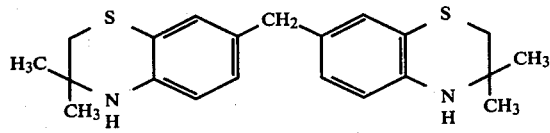

di-(3,3-dimethyl-2,3-dihydro-4H-1,4-benzothiazin-7-yl)-methane;
di-(2,2,3,3-tetramethyl-2,3-dihydro-4H-1,4-benzothiazin-7-yl)-methane

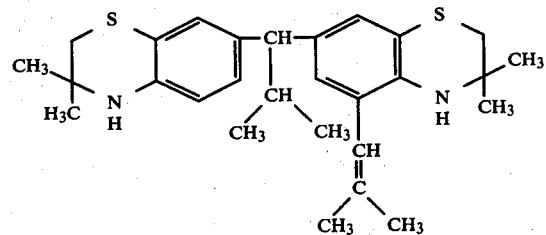

2-methyl-1-(3,3-dimethyl-2,3-dihydro-4H-1,4-benzothiazin-7-yl)-1-[3,3-dimethyl-5-(2-methyl-1-propenyl)-2,3-dihydro-4H-1,4-benzothiazin-7-yl]-propane
di-(3-methyl-8-nitro-3-phenyl-2,3-dihydro-4H-1,4-benzothiazin-7-yl)-methane
di-(3,3-diethyl-2,3-dihydro-5-stearoyl-4H-1,4-benzothiazin-7-yl)-methane
1,1-di-(3,3-dimethyl-2,3-dihydro-4H-1,4-benzothiazin-7-yl)-cyclohexane

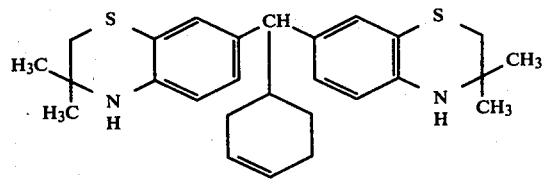

1-cyclohex-3-enyl-1,1-di-(3,3-dimethyl-2,3-dihydro-4H-1,4-benzothiazin-7-yl)-methane
1-(4-chlorophenyl)-1,1-di-(3,3-dimethyl-2-propyl-2,3-dihydro-4H-1,4-benzothiazin-7-yl)-methane

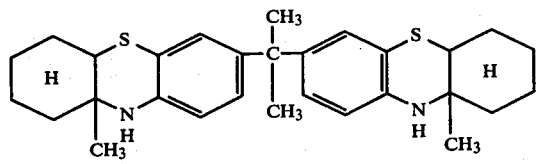

2,2-di-(10a-methyl-1,2,3,4,4a,10a-hexahydrophenothiazin-7-yl)-propane

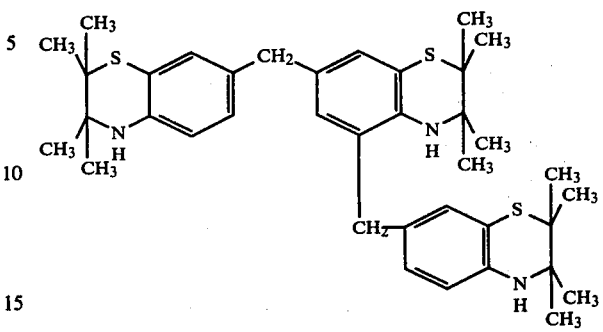

1-(2,2,3,3-tetramethyl-2,3-dihydro-4H-1,4-benzothiazin-7-yl)-1-[2,2,3,3-tetramethyl-5-(2,2,3,3-tetramethyl-2,3-dihydro-4H-1,4-benzothiazin-7-ylmethyl)-2,3-dihydro-4H-1,4-benzothiazin-7-yl]-methane.

The compounds corresponding to general formula (I) according to the present invention may be produced by reacting a compound corresponding to the following general formula (II):

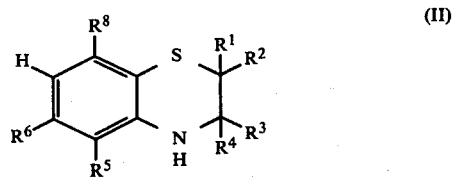

wherein the substituents are as defined above;
with a carbonyl compound corresponding to the following general formula (III):

wherein the substituents are as defined above;
in a molar ratio of from 10:1 to 1:1, optionally in an inert organic solvent and optionally in the presence of a catalyst at temperatures of from about 0° to about 200° C.

It is advantageous to use an acid catalyst, preferably a mineral acid. The reaction may be carried out in a solvent, such as ether, alcohol, toluene or carbon tetrachloride. The reaction may also be carried out in the absence of a solvent. The molar ratio between the compound (II) and the carbonyl compound (III) may vary from 10:1 to 1:1 and is preferably from 4:1 to 2:1. To shorten the reaction time, it is preferred to use elevated temperatures of from 50° to 150° C. or boiling temperature. For the same reason, it is advantageous in some cases to react the components under elevated pressure.

Compounds corresponding to general formula (I) wherein $R^5$ represents $C_1$–$C_{12}$ alkyl or $C_7$–$C_{11}$ aralkyl may also be produced by alkylating compounds (I) wherein $R^5$ represents hydrogen by reaction with olefins, styrene derivatives, alkyl halides, aralkyl halides, alcohols and the like in the presence of a Lewis acid catalyst. The reaction may be carried out in the absence of a solvent or in an inert solvent, such as ether, benzene, toluene, chlorobenzene, chloroform or carbon tetrachloride. Preferred Lewis acids are aluminium trichloride, boron trifluoride, anhydrous zinc chloride and concentrated sulphuric acid. The catalyst may be used in a quantity of from 0.001 to 110 mole percent, preferably from 0.1 to 10 mole percent. The temperature is from 20° to 200° C., preferably from 80° to 130° C. At relatively high temperatures in particular, it is preferred to carry out the reaction in the absence of oxygen.

Compounds corresponding to general formula (I) wherein $R^5$ represents an acyl radical are similarly obtained by acylating compounds (I) wherein $R^5$ represents hydrogen with carboxylic acid halides, anhydrides or with free carboxylic acids, but containing from 2 to 22, preferably from 10 to 18, carbon atoms, in the presence of a Lewis acid catalyst.

The compounds according to the present invention are suitable for stabilising organic polymers against thermo-oxidative degradation, particularly plastics, such as polyolefins, ABS-polymers, high-impact polystyrene, polyesters, polyamides, polycarbonates, polyurethanes, natural rubber, synthetic rubbers, such as butadiene-styrene copolymers, polybutadiene, polyisoprene, ethylene-propylene-diene terpolymers (EPDM-rubbers), butyl rubber, chlorinated and chlorosulphonated polyethylene and nitrile rubber.

One preferred application for the present compounds is in radically cross-linked polymers, particularly cross-linked polyethylene, but also ethylene/propylene copolymers and EPDM-rubbers, chlorinated and chlorosulphonated polyethylene.

The compounds according to the present invention are generally used in quantities of from 0.001 to 20%, preferably from 0.05 to 5%, based on the total weight of the polymer to be stabilised. The compounds may be introduced directly or through a master batch containing, for example, from 30 to 90% of a compound corresponding to general formula (I). The method of using master batches is known. The stabilised organic materials may only contain compounds corresponding to general formula (I) or additionally other auxiliaries for improving the properties thereof. Such auxiliaries are, for example, other stabilisers or co-stabilisers against deterioration under the effect of heat and oxygen or UV-light. Examples of co-stabilisers of this type are dilauryl and distearyl thiodipropionate, 2-mercaptobenzimidazole, 2,6-di-t-butyl-p-cresol, o-hydroxybenzophenone and the like. Other additives, such as anticorrosives and rust-proofing agents, dispersion aids, emulsifiers, plasticisers, lubricants, flameproofing agents and anitozonants, metal deactivators, blowing agents, coupling agents, dyes, pigments, fillers, carbon black, accelerators and cross-linking agents, may also be present.

The present invention also relates to the organic materials containing a compound corresponding to general formula (I) according to the present invention and also to an agent containing a compound corresponding to general formula (I).

The present invention is illustrated by the following Examples.

EXAMPLES

EXAMPLE 1

2.869 kg (16 moles) of 3,3-dimethyl-2,3-dihydro-4H-1,4-benzothiazine, 5 kg of methanol and 46 g (0.45 mole) of concentrated sulphuric acid are initially introduced, followed by the dropwise addition at 30° C. of 327 g (4 moles) of a 37% aqueous formaldehyde solution. After refluxing for 1.5 hours, 40 g (1 mole) of sodium hydroxide are added, followed by refluxing for another 3 hours. After cooling, the product is filtered under suction, the residue is washed with methanol and water and is dried in a recirculating air cabinet.

Di-(3,3-dimethyl-2,3-dihydro-4H-1,4-benzothiazin-7-yl)-methane melting at from 179° to 181° C. is obtained in a yield of 1.26 kg. The mass spectrum shows a molecular ion at 370 (100% relative intensity) and as main fragments 355 (90%), 192 (23%), 170 (20%) (stabiliser A).

EXAMPLE 2

The procedure is as in Example 1, except that isobutyraldehyde is added dropwise instead of formaldehyde. 2-methyl-1-(3,3-dimethyl-2,3-dihydro-4H-1,4-benzothiazin-7-yl)-1-[3,3-dimethyl-5-(2-methyl-1-propenyl)-2,3-dihydro-4H-1,4-benzothiazin-7-yl]-propane is obtained in the form of a tough resin. The mass spectrum shows a molecular ion at 466 (24% relative intensity) and as main fragments 423 (74%), 412 (14%), 369 (100%), 272 (19%), 178 (7%) (stabiliser B).

EXAMPLE 3

8.2 g of di-(2,2,3,3-tetramethyl-2,3-dihydro-4H-1,4-benzothiazin-7-yl)-methane are obtained as in Example 1 from 12 g of 2,2,3,3-tetramethyl-2,3-dihydro-4H-1,4-benzothiazine and 2.4 g of 37% formaldehyde solution. Its mass spectrum shows a molecular ion at 426 (94% relative intensity) and as main fragments 411 (18%) and 383 (100%). In addition, the product also contains small quantities of compounds containing 3 and 4 (2,2,3,3-tetramethyl-2,4-dihydro-4H-1,4-benzothiazine)-nuclei with molecular weights of 645 and 864.

EXAMPLE 4

90 g (0.5 mole) of 3,3-dimethyl-2,3-dihydro-4H-1,4-benzothiazine, 500 ml of toluene, 3.2 g of concentrated sulphuric acid and 27.5 g (0.25 mole) of tetrahydrobenzaldehyde are refluxed for 5 hours, washed with water, the organic phase dried and the solvent removed in vacuo. Unreacted 3,3-dimethyl-2,3-dihydro-4H-1,4-benzothiazine is distilled off under a high vacuum, leaving as residue 1-cyclohex-3-enyl-1,1-di-(3,3-dimethyl-2,3-dihydro-4H-1,4-benzothiazin-7-yl)-methane in the form of a dark brown brittle resin.

The mass spectrum shows a molecular ion at 450 (26% relative intensity) and as main fragments 370 (27%), 369 (100%) (stabiliser C).

EXAMPLE 5

Example 5 shows that the compounds according to the present invention are superior to phenolic stabilisers in natural rubber and are comparable in stabilising effect with the amine-containing anti-ager 2,2,4-trimethyl-1,2-dihydroquinoline oligomer.

The following mixture was prepared on mixing rolls:

|  | Parts, by weight |
|---|---|
| Light crepe | 100.0 |
| Zinc oxide | 10.0 |
| Stearic acid | 1.0 |
| Titanium dioxide | 10.0 |
| Blank fix | 60.0 |
| Tetramethyl thiuram disulphide | 0.5 |

-continued

| | Parts, by weight |
|---|---|
| Sulphur | 2.0 |
| Stabiliser as indicated in Table 1. | |

The mixture was press-vulcanised for 15 minutes at 130° C. The vulcanisate obtained was aged in an oxygen cylinder (according to Bierer-Davis) at 70° C. under an oxygen pressure of 21 bars (DIN 53 508).

The results are set out in Table 1 below.

TABLE 1

| | Without stabiliser (Comp. 1) | Mixture of alkyl and aralkyl phenols (Comp. 2) | 2,2,4-trimethyl-1,2-dihydroquin-oline oligomer (Comp. 3) | A | B | C |
|---|---|---|---|---|---|---|
| Parts, by weight | — | 1 | 1 | 1 | 1 | 1 |
| Before ageing | | | | | | |
| Strength (MPa) | 22.7 | 23.1 | 23.8 | 20.4 | 21.5 | 23.3 |
| Elongation (%) | 730 | 730 | 710 | 730 | 780 | 720 |
| Modulus at 450% Elongation (MPa) | 8.1 | 8.0 | 9.6 | 5.9 | 6.9 | 9.0 |
| Elasticity (%) at 20° C. | 74 | 74 | 75 | 69 | 69 | 72 |
| at 70° C. | 79 | 81 | 81 | 72 | 75 | 77 |
| Hardness (Shore A) at 20° C. | 52 | 52 | 54 | 47 | 47 | 52 |
| at 70° C. | 52 | 52 | 53 | 47 | 44 | 52 |
| After ageing for 7 days | | | | | | |
| Strength (MPa) | 5.0 | 14.6 | 16.8 | — | 16.8 | 16.3 |
| Elongation (%) | 470 | 600 | 580 | — | 650 | 590 |
| Modulus at 450% Elongation (MPa) | — | 8.9 | 11.5 | — | 8.9 | 10.5 |
| Elasticity (%) at 20° C. | — | 65 | 72 | — | 63 | 63 |
| at 70° C. | 50 | 69 | 79 | — | 70 | 71 |
| Hardness (Shore A) at 20° C. | 47 | 52 | 56 | — | 48 | 54 |
| at 70° C. | 35 | 50 | 55 | — | 47 | 51 |
| After ageing for 14 days | | | | | | |
| Strength (MPa) | destroyed | 9.3 | 14.4 | 13.4 | 13.5 | 12.7 |
| Elongation (%) | | 560 | 570 | 570 | 620 | 580 |
| Modulus at 450% elongation (MPa) | | 7.1 | 10.4 | 8.3 | 8.9 | 9.3 |
| Elasticity at 20° C. | | 47 | 66 | 60 | 58 | 57 |
| at 70° C. | | 56 | 75 | 70 | 66 | 70 |
| Hardness (Shore A) at 20° C. | | 46 | 54 | 48 | 47 | 52 |
| at 70° C. | | 38 | 53 | 46 | 45 | 50 |
| After ageing for 21 days | | | | | | |
| Strength (MPa) | destroyed | destroyed | 11.9 | 10.5 | 11.4 | 8.0 |
| Elongation (%) | | | 540 | 550 | 600 | 520 |
| Modulus at 450% elongation (MPa) | | | 9.8 | 7.0 | 7.7 | 7.1 |
| Elasticity (%) at 20° C. | destroyed | destroyed | 55 | 57 | 51 | 49 |
| at 70° C. | | | 63 | 66 | 58 | 58 |
| Hardness (Shore A) at 20° C. | | | 53 | 49 | 45 | 49 |
| at 70° C. | | | 50 | 47 | — | 40 |

Vulcanisates containing comparison substances 1 and 2 of Table 1, 2,2'-methylene-bis-6-t-butyl-4-methyl-phenol (comparison 4) and stabiliser A did not show any discolouration before exposure to the light, while vulcanisates containing comparison substance 3 had already turned pink. After 2 months in daylight, the vulcanisates containing comparison substances 1 and 2 had remained white, the vulcanisate containing stabiliser A had turned pale cream, the vulcanisate containing comparison substance 4 had turned pink, while the vulcanisate containing comparison substance 3 had turned light brown. Accordingly, the compounds according to the present invention are equivalent to the phenolic antioxidants (comparison substances 1, 2 and 4) in the extent to which they discolour the vulcanisates and cause distinctly less discolouration of the vulcanisates than amine-containing anti-agers (comparison substance 3).

EXAMPLE 6

EPDM cable mixtures having the following compositions were prepared:

TABLE 2

| | Parts, by weight | |
|---|---|---|
| EPDM-rubber[1] | 50 | 50 |
| EPDM-rubber[2] | 50 | 50 |
| Kaolin | 150 | 150 |
| Vinyl silane | 1 | 1 |
| Polyethylene anti-ozonant wax | 10 | 10 |
| 2,2,4-trimethyl-1,2-dihydroquinoline, polym. | 1 | — |
| Stabiliser A | — | 1 |
| Paraffin | 5 | 5 |
| Mineral oil plasticiser | 30 | 30 |
| Triallyl cyanurate | 1.5 | 1.5 |
| Zinc oxide | 5 | 5 |
| Dicumyl peroxide, 40% | 5 | 5 |
| Before ageing: | | |
| Strength (MPa) | 7 | 6.1 |
| Breaking elongation (%) | 310 | 300 |
| Modulus at 100% elongation (MPa) | 3 | 3.1 |
| Modulus at 300% elongation (MPa) | 7 | 6.1 |
| Hardness at 20° C. (Shore A) | 72 | 69 |
| After ageing for 10 days in hot air at 100° C. | | |
| Strength (MPa) | 6.9 | 6.3 |
| Breaking elongation (%) | 310 | 300 |
| Hardness at 20° C. (Shore A) | 70 | 69 |
| After ageing for 7 days in hot air at 135° C. | | |
| Strength (MPa) | 8.8 | 7.5 |
| Breaking elongation (%) | 330 | 290 |

TABLE 2-continued

| | Parts, by weight | |
|---|---|---|
| Hardness at 20° C. (Shore A) | 77 | 74 |

[1] Statistical EPDM containing ethylidene norbornene as the ter component and having a Mooney viscosity ML 1 + 4 at 100° C. of 70.
[2] Sequential EPDM containing ethylidene norbornene as ter component and having a high crude polymer strength and a Mooney viscosity ML 1 + 4 at 100° C. of 85.

It may be seen from Table 2 that stabiliser A is as effective as an anti-ager as the slightly discolouring 2,2,4-trimethyl-1,2-dihydroquinoline oligomer.

EXAMPLE 7

The following natural latex mixture was prepared:

| | Parts, by weight |
|---|---|
| Natural latex | 167 |
| 3-benzyl-4-hydroxybiphenylpolyglycol ether, 20% | 1 |
| Zinc oxide, active | 2.5 |
| Colloidal sulphur | 1.8 |

The dispersion was prepared using either a ball mill or an "Ultraturax." The sample was vulcanised for 15 minutes at 110° C. and then aged in hot air at 100° C. The results are set out in Table 3.

bars were then injection moulded from the thus-obtained mixture.

Impact strength $a_n$ was measured in accordance with DIN 53 453 before and after heating from 4 minutes by the heating unit of a hot vacuum forming machine (Illig U 60; distance from the surface of the standrad test bars to the IR lamp = 15 cm). Notched impact strength was also measured before the heat treatment. The results set out in Table 4 demonstrate the good stabilising effect of the compound according to the present invention.

TABLE 4

| Test | Stabiliser | Impact strength $a_n$ before ageing | Impact strength $a_n$ after under heat | Notched impact strength $a_k$ (KJ/m²) |
|---|---|---|---|---|
| A | — | unbroken | 37 KJ/m² | 17 |
| B | 0.2% of 2,2'-dihydroxy-3,3'-dicyclohexyl-5,5'-dimethyl diphenyl methane (prior art) | " | unbroken | 20 |
| C | 0.5% of 2,2'-dihydroxy-3,3'-dicyclohexyl-5,5'-dimethyl diphenyl methane (prior art) | " | " | 18 |
| D | 0.2% of stabiliser A | " | " | 19 |
| E | 0.5% of stabiliser A | " | " | 19 |

TABLE 3

| | Comp. 1 | Comp. 2 | Comp. 3 | Comp. 4 | Example A | Example B | Comp. 5 | Comp. 6 |
|---|---|---|---|---|---|---|---|---|
| 2,2,4-trimethyl-1,2-dihydro quinoline (parts, by weight) | 1 | 1 | 0.5 | 0.5 | — | — | — | — |
| 2-mercaptobenzimidazole (parts, by weight) | — | — | 0.5 | 0.5 | 0.5 | 0.5 | — | — |
| Stabiliser A | — | — | — | — | 0.5 | 0.5 | — | — |
| Styrenised diphenylamine (parts, by weight) | — | — | — | — | — | — | 1 | — |
| Dispersion using a ball mill | + | — | + | — | + | — | + | + |
| Dispersion using an "Ultraturax" | — | + | — | + | — | + | — | — |
| Stability of the mixture in storage after 14 days | slightly speckly | slightly speckly | thixo-tropic | thixo-tropic and slightly speckly | satis-factory | sediments after stirring slightly speckly | satis-factory | satis-factory |
| Before ageing | | | | | | | | |
| Tensile strength (Kp/cm²) | 193 | 240 | 187 | 242 | 204 | 199 | 234 | 195 |
| Breaking elongation (%) | 685 | 695 | 760 | 705 | 745 | 710 | 695 | 720 |
| Modulus at 500% elongation (Kp/cm²) | 52 | 50 | 27 | 40 | 39 | 41 | 44 | 29 |
| After ageing for 3 days | | | | | | | | |
| Tensile strength (Kp/cm²) | 47 | 25 | 100 | 77 | 55 | 78 | 34 | 8 |
| Breaking elongation (%) | 430 | 465 | 555 | 430 | 565 | 485 | 555 | 260 |
| Modulus at 500% elongation (Kp/cm²) | — | — | 41 | — | — | — | — | — |
| After ageing for 6 days | | | | | | | | |
| Tensile strength (Kp/cm²) | 10 | 8 | 21 | 13 | 36 | 17 | 10 | 7 |
| Breaking elongation (%) | 140 | 90 | 270 | 195 | 380 | 305 | 190 | 70 |
| Modulus at 500% elongation (Kp/cm²) | — | — | — | — | — | — | — | — |

Table 3 demonstrates the superiority of the compound according to the present invention (stabiliser A) over the comparison compounds in terms of its anti-ageing effect and dispersibility in the latex.

EXAMPLE 8

The quantities of stabiliser indicated in Table 5 were additionally worked by means of a 3 kg laboratory internal kneader of the Banbury type into an ABS commercial product normally stabilised for standard applications in which the monomer ratio of acrylonitrile to butadiene to styrene was 20:32:48% by weight and in which the SAN-resin phase had an average molecular weight of from 110,000 to 160,000. Standard small test

EXAMPLE 9

After the indicated quantities of stabiliser together with 1.5% of di-t-butyl peroxide had been worked into a high-pressure polyethylene base resin for LPDE cable insulation (MI=2.6 g/10 mins at 190° C.; d=0.922 g/cc), 1 mm thick sheets were produced by moulding and cross-linked at 135° C. S2 standard bars were then punched out and subjected to ageing in hot air at 150° C.

The results are set out in Table 5 and demonstrate the advantage of the compound according to the present invention.

TABLE 5

|  |  | Before ageing at 150° C. | After 10 | 20 | 40 | 100 days |
|---|---|---|---|---|---|---|
| 0.3% of 2,2,4-trimethyl-1,2-dihydroquinoline oligomer (Comparison 1) Gel content: 91% | tensile strength (MPa) | 21.4 | 10.3 | 6.2 | destroyed | destroyed |
|  | elongation (%) | 445 | 218 | — | — | — |
| 1.5% of 2,2,4-trimethyl-1,2-dihydroquinoline oligomer (Comparison 2) Gel content: 92% | tensile strength (MPa) | 18.9 | 14.2 | 12.9 | 4.8 | destroyed |
|  | elongation (%) | 457 | 406 | 316 | 32 | — |
| 0.3% of stabiliser A | tensile strength (MPa) | 27.8 | 20.2 | 17.4 | 9.5 | 8.4 |
| Gel content: 89% | elongation (%) | 580 | 494 | 462 | 95 | 92 |
| 0.5% of stabiliser A | tensile strength (MPa) | 26.5 | 21.2 | 18.4 | 12 | 9 |
| Gel content: 85% | elongation | 582 | 519 | 484 | 347 | 136 |

The following results were obtained in the so-called "hot set test" according to VDE 0472:

| Sample containing 0.5% of stabiliser A | 150° C./0.2 MPa: 68% elongation 200° C./0.2 MPa: 70% elongation |
|---|---|
| Sample containing 0.5% of 2,2,4-trimethyl-1,2-dihydroquinoline oligomer (Comparison) | 150° C./0.2 MPa: 39% elongation 200° C./0.2 MPa: 26% elongation |

In this test, too, the compound according to the present invention shows a considerably better effect.

EXAMPLE 10

0.5% of the stabiliser indicated was worked into an ethylene/vinyl acetate copolymer base resin for LDPE cable insulations (MI=25 g/10 mins. at 190° C.; d=0.930 g/cc; vinyl acetate content 9%) and 1 mm thick sheets were moulded from the resulting compound. The thus-produced sheets were then cross-linked using a van-der-Graaf generator (radiation dose 20 Mrad), after which S2 standard bars were punched out and subjected to ageing in hot air at 150° C.

The results set out in Table 6 demonstrate the advantages of the compound according to the present invention.

TABLE 6

|  |  | After 0 | 20 | 60 days' ageing |
|---|---|---|---|---|
| 0.5% of 2,2,4-trimethyl-1,2-dihydroquinoline oligomer (comparison) Gel content: 75% | tensile strength (MPa) | 28 | 2.9 | destroyed |
|  | elongation (%) | 499 | 6 | — |
| 0.5% of stabiliser A | tensile strength (MPa) | 26.9 | 8.5 | 7.1 |
| Gel content: 78% | elongation (%) | 549 | 209 | 80 |

The compound according to the present invention is also superior in the hot set test according to VDE 0472:

| LDPE containing 0.5% of stabiliser A | 150° C./0.2 MPa 105% elongation 200° C./0.2 MPa 65% elongation |
|---|---|

EXAMPLE 11

0.5% of stabiliser, 1.5% of vinyl trimethoxy silane, 0.15% of dicumyl peroxide and 0.05% of dibutyl tin dilaurate were worked into a high pressure polyethylene base resin for LDPE cable insulations and 1 mm thick sheets were moulded from the resulting compound. After cross-linking under the effect of boiling water for 3 hours, S2 standard bars were punched out and subjected to ageing in hot air at 150° C.

The results set out in Table 7 demonstrate the effectiveness of the compound according to the present invention.

TABLE 7

|  |  | After 0 | 10 | 30 days' ageing |
|---|---|---|---|---|
| 0.5% of 2,2,4-trimethyl-1,2-dihydroquinoline oligomer (comparison) | tensile strength (MPa) | 15 | 15.3 | 6.7 |
|  | elongation (%) | 310 | 353 | 12 |
| 0.5% of stabiliser A | tensile strength (MPa) | 18.2 | 17 | 6 |
|  | elongation (%) | 510 | 430 | 35 |

We claim:
1. A compound of the formula

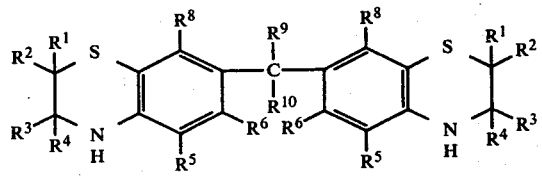

wherein
R$^1$ and R$^2$, which may be the same or different, each represents hydrogen, lower alkyl containing from 1 to 4 carbon atoms, cycloalkyl containing from 5 to 8 carbon atoms, aralkyl containing from 7 to 11 carbon atoms or carbocyclic aryl having 6 carbon atoms or together represent a radical —(CH$_2$)$_m$— wherein m represents an integer of from 4 to 7;
R$^3$ and R$^4$ which may be the same or different, each represents lower alkyl containing from 1 to 4 carbon atoms, cyclohexyl, aralkyl containing from 7 to 11 carbon atoms or carbocyclic aryl having 6 carbon atoms or together represent a radical —(CH$_2$)$_n$— wherein n represents an integer of from 4 to 7, or one of the radicals R$^3$ or R$^4$ together with $R^1$ or $R^2$ represents an alkylene radical containing from 3 to 6 carbon atoms;

$R^6$ and $R^8$, which may be the same or different, each represents hydrogen, halogen, nitro, linear or branched alkyl containing from 1 to 12 carbon atoms, linear or branched alkenyl containing from 2 to 12 carbon atoms, aralkyl containing from 7 to 11 carbon atoms, cycloalkyl containing from 5 to 8 carbon atoms, and the radicals $R^5$ are the same or different and represent hydrogen, halogen, nitro, linear or branched alkyl containing from 1 to 12 carbon atoms, linear or branched alkenyl containing from 2 to 12 carbon atoms, cycloalkyl containing from 5 to 8 carbon atoms, aralkyl containing from 7 to 11 carbon atoms, alkoxy, the radical

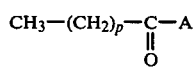

wherein p represents an integer of from 0 to 20, preferably from 8 to 16, and

A represents $-(CH_2)_q-$, $-O-(CH_2)_q-$, $-NH-(CH_2)_q-$ or $-S-(CH_2)_q$ q=0 to 4, preferably 0 or 1, or the radical

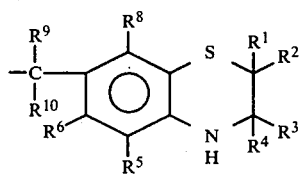

wherein $R^1$ to $R^6$ and $R^8$ are as defined above, while $R^9$ and $R^{10}$ represent the radicals defined below, and $R^9$ and $R^{10}$ independently represent hydrogen, carbocyclic aryl having 6 carbon atoms, linear or branched alkyl containing from 1 to 12 carbon atoms, cycloalkyl or cycloalkenyl containing from 5 to 8 carbon atoms or $R^9$ and $R^{10}$ together with the carbon atoms to which they are attached complete a cycloalkyl radical containing from 5 to 7 carbon atoms.

2. A compound of claim 1 wherein $R^1$ and $R^2$ are hydrogen or a $C_1-C_4$-alkyl radical; $R^3$ and $R^4$ are a $C_1-C_4$-alkyl radical; $R^5$, $R^6$ and $R^8$ are each hydrogen and $R^9$ and $R^{10}$ are as defined in claim 1.

3. A compound of claim 1 wherein $R^1$ and $R^2$ are each hydrogen or methyl; $R^3$ and $R^4$ are each methyl; $R^5$, $R^6$ and $R^8$ are each hydrogen and $R^9$ and $R^{10}$ are as defined in claim 1.

4. The compound

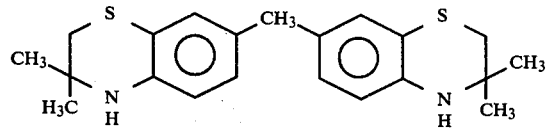

5. A process for the production of a compound of claim 1 wherein a compound of the formula

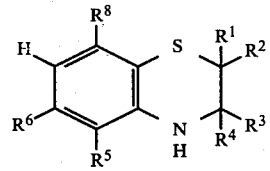

wherein $R^1$ to $R^6$ and $R^8$ are as defined in claim 1 is reacted with a compound of the formula

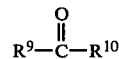

wherein $R^9$ and $R^{10}$ are as defined in claim 10 in a molar ratio of from 10:1 to 1:1 at a temperature of from 0° to 200° C.

6. The process of claim 5 wherein said reaction is carried out in the presence of a catalytic amount of an acid catalyst.

7. The process of claim 5 wherein said reaction is carried out in an inert solvent.

* * * * *